(12) United States Patent
Dennison et al.

(10) Patent No.: US 10,369,054 B2
(45) Date of Patent: *Aug. 6, 2019

(54) VARYING A NUMERICAL APERTURE OF A LASER DURING LENS FRAGMENTATION IN CATARACT SURGERY

(71) Applicant: AMO Development, LLC, Santa Ana, CA (US)

(72) Inventors: Anthony W. Dennison, Irvine, CA (US); Michael A. Campos, Fremont, CA (US); Hong Fu, Pleasanton, CA (US)

(73) Assignee: AMO Development, LLC, Santa Ana, CA (US)

(*) Notice: Subject to any disclaimer, the term of this patent is extended or adjusted under 35 U.S.C. 154(b) by 377 days.

This patent is subject to a terminal disclaimer.

(21) Appl. No.: 15/200,768

(22) Filed: Jul. 1, 2016

(65) Prior Publication Data
US 2016/0310320 A1    Oct. 27, 2016

Related U.S. Application Data

(62) Division of application No. 14/193,740, filed on Feb. 28, 2014, now Pat. No. 9,393,156.
(Continued)

(51) Int. Cl.
*A61F 9/008* (2006.01)

(52) U.S. Cl.
CPC ........ *A61F 9/0084* (2013.01); *A61F 9/00825* (2013.01); *A61F 2009/0087* (2013.01);
(Continued)

(58) Field of Classification Search
None
See application file for complete search history.

(56) References Cited

U.S. PATENT DOCUMENTS

| 4,764,930 A | 8/1988 | Bille et al. |
| 5,825,958 A * | 10/1998 | Gollihar ............... A61B 18/22 |
| | | 385/125 |

(Continued)

FOREIGN PATENT DOCUMENTS

| DE | 19940712 A1 | 3/2001 |
| DE | 102005013949 A1 | 9/2006 |
| DE | 102011006085 A1 | 9/2012 |

OTHER PUBLICATIONS

Ayaki et al, Size of the lens nucleus separated by hydrodissection, Ophthalmic Surg. Jul. 1993;24(7):492-3.*
(Continued)

*Primary Examiner* — Michael W Kahelin
*Assistant Examiner* — Qingjun Kong
(74) *Attorney, Agent, or Firm* — Johnson & Johnson Surgical Vision, Inc.

(57) ABSTRACT

Some embodiments disclosed here provide for a method fragmenting a cataractous lens of a patient's eye using an ultra-short pulsed laser. The method can include determining, within a lens of a patient's eye, a high NA zone where a cone angle of a laser beam with a high numerical aperture is not shadowed by the iris, and a low NA zone radially closer to the iris where the cone angle of the laser beam with a low numerical aperture is not shadowed by the iris. Laser lens fragmentation is accomplished by delivering the laser beam with the high numerical aperture to the high NA zone, and the laser beam with the low numerical aperture to the low NA zone. This can result in a more effective fragmentation of a nucleus of the lens without exposing the retina to radiation above safety standards.

8 Claims, 9 Drawing Sheets

Related U.S. Application Data

(60) Provisional application No. 61/794,359, filed on Mar. 15, 2013.

(52) U.S. Cl.
CPC ............... *A61F 2009/00851* (2013.01); *A61F 2009/00863* (2013.01); *A61F 2009/00887* (2013.01)

(56) References Cited

U.S. PATENT DOCUMENTS

| | | | |
|---|---|---|---|
| 5,993,438 A | 11/1999 | Juhasz et al. | |
| 2007/0189664 A1* | 8/2007 | Andersen | A61B 3/0008 385/25 |
| 2008/0015556 A1* | 1/2008 | Chan | A61B 18/203 606/9 |
| 2009/0171327 A1* | 7/2009 | Kurtz | A61F 9/008 606/6 |
| 2010/0191226 A1* | 7/2010 | Blumenkranz | A61F 9/00736 606/4 |
| 2011/0028953 A1* | 2/2011 | Raksi | A61F 9/008 606/4 |
| 2013/0237972 A1* | 9/2013 | Raksi | A61F 9/00825 606/6 |

OTHER PUBLICATIONS

Delori F.C., et al., "Maximum Permissible Exposures for Ocular Safety (Ansi 2000), With Emphasis on Ophthalmic Devices," Journal of the Optical Society of America. A, Optics, Image Science, and Vision, 2007, vol. 24 (5), pp. 1250-1265.

International Search Report and Written Opinion for Application No. PCT/US2014/019449, dated May 22, 2014, 12 pages.

Michael R., et al., "The Ageing Lens and Cataract: A Model of Normal and Pathological Ageing," Philosophical Transactions of the Royal Society B: Biological Science, 2011, vol. 366 (1568), pp. 1278-1292.

Voke J., et al., "Radiation Effects on the Eye, Part 1—Infrared Radiation Effects on Ocular Tissue," Optometry Today, 1999, pp. 22-28.

* cited by examiner

VARYING A NUMERICAL APERTURE OF A LASER DURING LENS FRAGMENTATION IN CATARACT SURGERY

CROSS REFERENCE TO RELATED APPLICATIONS

This application is a divisional of and claims priority to U.S. patent application Ser. No. 14/193,740, filed Feb. 28, 2014, which claims the benefit of priority to U.S. Provisional Application No. 61/794,359, filed Mar. 15, 2013, the entire contents of which are incorporated herein by reference.

BACKGROUND

Field

Embodiments of this invention generally relate to laser cataract surgery, and more particularly to a method of laser-assisted lens fragmentation.

Description of Related Art

Eye disease can impair a patient's vision. For example, a cataract can increase the opacity of an ocular lens, and eventually, cause blindness. To restore the patient's vision, the diseased lens may be surgically removed and replaced with an artificial lens, known as an intraocular lens, or IOL. A number of medically recognized techniques are utilized for removing a cataractous lens based on, for example, phacoemulsification, mechanical cutting or destruction, laser treatments, water jet treatments, and so on.

A typical cataract surgery involves removing the eye's natural lens while leaving in place the back of the capsule which holds the lens in place. Using certain procedures, such as laser treatments along with phacoemulsification, for example, the cataract can be broken into tiny pieces that can be removed from the eye through a relatively small incision. In cataract surgery using phacoemulsification, the surgeon makes a small incision in the white portion of the eye near the outer edge of the cornea. An ultrasonic probe is then inserted through this opening and ultrasonic frequencies are used to break up the cataract into tiny pieces. The emulsified material can be simultaneously suctioned from the eye, typically using the open tip of the same instrument. To reduce the amount of ultrasonic energy used to break up the cataract, the lens can be softened and/or fragmented using a laser prior to application of ultrasonic energy. As such, the hard central core of the cataract (the nucleus) is removed first, followed by extraction of the softer, peripheral cortical fibers that make up the remainder of the lens. As compared to other forms of cataract surgery, laser-assisted cataract provides faster healing and rehabilitation as well as reduced discomfort.

SUMMARY

In laser-assisted cataract surgery, laser lens fragmentation can be used to pre-cut or fragment the eye lens before it is removed. A surgical laser, such as a non-ultraviolet, ultra-short pulsed laser that emits radiation with pulse durations as short as nanoseconds and femtoseconds (e.g., a femtosecond laser, or a picosecond laser) can be used to cut the lens of the patient's eye into pieces. These pieces can then be removed through a small incision in the eye. Typically, to reduce the overall amount of energy delivered to the eye surgery, laser lens fragmentation is performed prior to phacoemulsification. Laser systems capable of generating ultra-short pulsed laser beams are disclosed in for example, U.S. Pat. Nos. 4,764,930 and 5,993,438, which are incorporated here by reference. In some situations, fragmenting a lens with a laser can reduce the amount of cumulative dispersive energy (CDE) used for phacoemulsification than is used for a non-laser-treated cataractous lens. The reduction in CDE can depend at least in part on the grade of the cataract, where a higher grade cataract can be more difficult to cut and/or remove. For example, laser lens fragmentation may be able to completely fragment a grade 1 nuclear cataract (e.g., no phacoemulsification required, or a 100% reduction in CDE), while CDE may be reduced by about 40% to 50% for a grade 4 nuclear cataract. A reduction in the amount of CDE during phacoemulsification can generally be desirable because phacoemulsification can be one of the key causes of complications related to cataract surgery, including for example, posterior capsular breaks and/or corneal edema.

One limitation on the efficacy of laser lens fragmentation for higher-grade nuclear cataracts may be related to safety standards. Regulations place limits on the amount of energy that can be delivered to the retina of a patient's eye, and these limits are based at least in part on safety considerations. The limits are designed to reduce or prevent permanent or debilitating damage to the retina during laser procedures. The amount of energy or power delivered to the retina during a laser procedure is based at least in part on the energy of the laser and a numerical aperture of the laser beam.

Another factor affecting the efficacy of laser lens fragmentation is related to shadowing effects by the iris. The extent of the volume of tissue that can be treated using a laser beam can depend at least in part on a desire to not deliver laser energy to the iris. When a laser is focused onto a targeted focal spot, the incoming laser beam has a substantially conical shape. Hence, the larger the numerical aperture of the laser beam, the larger is the opening angle of the cone. Accordingly, when the target volume is past the iris, the potential treatment volume decreases as the numerical aperture of the laser beam increases.

Typical systems and methods have been designed to find a balance between safety, iris shadowing, laser lens fragmentation efficacy, cost, and complexity. To increase or maximize the treatment volume, these systems and methods generally use a relatively low numerical aperture (e.g., about 0.125) of the laser beam. The choice of the relatively low numerical aperture affects the maximum amount of laser energy that can be used, because, as described, a reduction in numerical aperture increases the energy delivered to the retina for a given laser energy. The relatively low numerical aperture and the resultant laser energy affect how effectively the laser fragments a nucleus of a cataract. For example, using a relatively low numerical aperture, some of the more effective laser cataract surgery systems have been able to reduce the amount of CDE during phacoemulsification for grade 3 or 4 nuclear cataracts by about 40% to about 50%.

Embodiments of the systems and methods described here can increase the efficacy and efficiency of laser lens fragmentation and/or reduce the amount of CDE used for ultrasonic-breaking of cataracts by using a laser beam with a numerical aperture that varies as a function of a targeted location within the lens. By using a relatively high numerical aperture in a central region of the lens and a relatively low numerical aperture in a peripheral region of the lens, the potential treatment volume can be the same, or greater than, previous systems' treatment volume while applying a greater amount of energy to the nucleus of the cataract. This can result in a greater efficacy in breaking or fragmenting cataracts, and particularly high grade nuclear cataracts, thereby reducing the amount of CDE during phacoemulsification, or eliminating the need for phacoemulsification altogether.

In one aspect, the embodiments disclosed here provide for systems and methods for fragmenting a lens by varying a numerical aperture of a laser beam. In a first, central region of the lens, a relatively high numerical aperture laser beam is used, and in a second, peripheral region of the lens, a lower numerical aperture laser beam is used. The high numerical aperture laser beam can be used to focus more energy in the central region of the lens, where cataracts can be more difficult to fragment. The higher energy can be due at least in part to a greater amount of energy at the focus of the laser beam. The higher energy of the high numerical aperture laser beam can also be configured to not violate safety restrictions, as the higher numerical aperture delivers less power to the retina than a lower numerical aperture laser beam with comparable energy. The low numerical aperture laser beam can be used near the iris to increase the treatment volume without delivering laser energy to the iris. The low numerical aperture laser beam can be configured to effectively fragment this portion of the lens using less energy than the high numerical aperture laser beam due at least in part to cataracts being typically softer and easier to fragment near the periphery. Accordingly, the method can be used to more effectively fragment a lens within a similar volume when compared to conventional systems.

In another aspect, a method of performing a laser lens fragmentation procedure is provided where the method includes measuring features of an eye of a patient to find a total laser treatment region. The method includes determining: a safety zone comprising a region of the eye of the patient which will not receive focused laser radiation; a high numerical aperture ("NA") zone, the high NA zone comprising a region where a cone angle of a laser beam with a high numerical aperture is not shadowed by an iris of the patient's eye; and a low NA zone, the low NA zone comprising a region radially closer to the iris than the high NA zone where the cone angle of the laser beam with a low numerical aperture is not shadowed by the iris. The method includes performing laser lens fragmentation by delivering the laser beam with the high numerical aperture to the high NA zone, and delivering the laser beam with the low numerical aperture to the low NA zone. In the method, the high NA zone, the low NA zone, and the safety zone can be configured to occupy, in aggregate, approximately the entirety of the total laser treatment region.

In some implementations, the high numerical aperture is greater than or equal to about 0.25 and/or the low numerical aperture is less than or equal to about 0.15. In some implementations, measuring features of an eye of a patient includes measuring a pupil diameter, an anterior boundary, or a posterior boundary of a lens of the patient's eye.

In some implementations, the safety zone is a region of the lens of the patient's eye that includes a volume that is at least about 0.5 mm inwards from an edge of an iris of the patient's eye and at least about 0.5 mm from an anterior lens capsule and at least about 0.5 mm from a posterior lens capsule.

In another aspect, a laser cataract surgery control system is provided. The system includes a controller comprising one or more physical processors. The system also includes a fragmentation module configured to use the one or more physical processors to determine a laser lens fragmentation treatment plan. To determine the laser fragmentation treatment plan, the laser fragmentation module determines a first region of a lens of a patient's eye to receive a laser beam having a first numerical aperture and a second region of the lens of the patient's eye to receive a laser beam having a second numerical aperture, the second numerical aperture being lower than the first numerical aperture, and the second region being radially closer, on average, to an iris of the patient's eye than the first region. The system includes a laser control module in communication with a laser source. The laser control module is configured to control the laser source to deliver the laser beam having the first numerical aperture and a first energy to the first region of the lens, and to control the laser source to deliver the laser beam having the second numerical aperture and a second energy to the second region of the lens. The first numerical aperture and the first energy are configured to deliver a first peak laser energy to a retina of the patient's eye that is less than or equal to a safety threshold.

In some implementations, the second numerical aperture and the second energy are configured to deliver a second peak laser energy to the retina that is less than or equal to a safety threshold. In some embodiments, the safety threshold is determined based at least partly on a safety standard involving a maximum permissible radiant exposure. In some implementations, the safety standard conforms to ANSI Z136.1-2000 Standard.

In some implementations, the system further includes an image processing module in communication with an imaging system. The image processing module is configured to: receive an image of the patient's eye; determine, using the at least one physical processor, a size of a pupil of the patient's eye; and determine, using the at least one physical processor, a relative location and size of the lens of the patient's eye. In some implementations, the imaging system is an optical coherence tomography system. In some implementations, the fragmentation module is configured to receive the size of the pupil and the size of the lens of the patient's eye from the image processing module, wherein the fragmentation module is configured to use the size of the pupil and the size of the lens to determine the first region and the second region.

In some implementations, the first region is configured to maximize a volume in the lens where the laser beam having the first numerical aperture is used to perform laser lens fragmentation, wherein a maximum radius of the first region from the center of the lens of the patient's eye is determined by a shadowing effect caused by the iris of the patient's eye.

In some implementations, the fragmentation module is further configured to determine a third region of the lens of the patient's eye to receive the laser beam having a third numerical aperture, the third region being between the first region and the second region, and the third numerical aperture being less than the first numerical aperture and greater than the second numerical aperture.

In some implementations, the first numerical aperture is equal to about 0.3 and/or the second numerical aperture is equal to about 0.125. In some implementations, after delivery of the laser beam with the first numerical aperture to the first region, and after delivery of the laser beam with the second numerical aperture to the second region, the lens of the patient's eye is sufficiently fragmented such that no phacoemulsification is required to remove the fragmented portion of the lens.

In another aspect, a method of performing a laser lens fragmentation procedure is provided. The method includes determining, using at least one physical processor, a first region of a lens of a patient's eye to receive a laser beam having a first numerical aperture. The method includes determining, using the at least one physical processor, a second region of the lens of the patient's eye to receive a laser beam having a second numerical aperture, the second numerical aperture being lower than the first numerical aperture, and the second region being radially closer, on average, to an iris of the patient's eye than the first region. The method includes controlling a laser source to deliver the laser beam having the first numerical aperture and a first energy to the first region of the lens. The method includes controlling the laser source to deliver the laser beam having the second numerical aperture and a second energy to the second region of the lens. The first numerical aperture and the first energy are configured to deliver a peak laser energy to a retina of the patient's eye that is less than a safety threshold.

In some implementations, after delivery of the laser beam with the first numerical aperture to the first region and after delivery of the laser beam with the second numerical aperture to the second region, the lens of the patient's eye is sufficiently fragmented such that no phacoemulsification is required to remove the fragmented portion of the lens. In a further implementation, the lens of the patient's eye comprises a grade 3 nuclear cataract.

BRIEF DESCRIPTION OF THE DRAWINGS

Details of one or more implementations of the subject matter described in this specification are set forth in the accompanying drawings and the description below. Other features, aspects, and advantages will become apparent from the description, the drawings, and the claims. The drawings depicting novel and non-obvious aspects of the invention are for illustrative purposes only. Note that the relative dimensions of the following figures may not be drawn to scale. The drawings include the following figures in which like numerals refer to like parts.

DETAILED DESCRIPTION

It is to be understood that the figures and descriptions of the present invention have been simplified to illustrate elements that are relevant for a clear understanding of the present invention, while eliminating, for the purpose of clarity, many other elements found in typical laser cataract surgery systems. Those of ordinary skill in the arts can recognize that other elements and/or steps are desirable and may be used in implementing the embodiments described here.

Laser Lens Fragmentation

Figure 1:
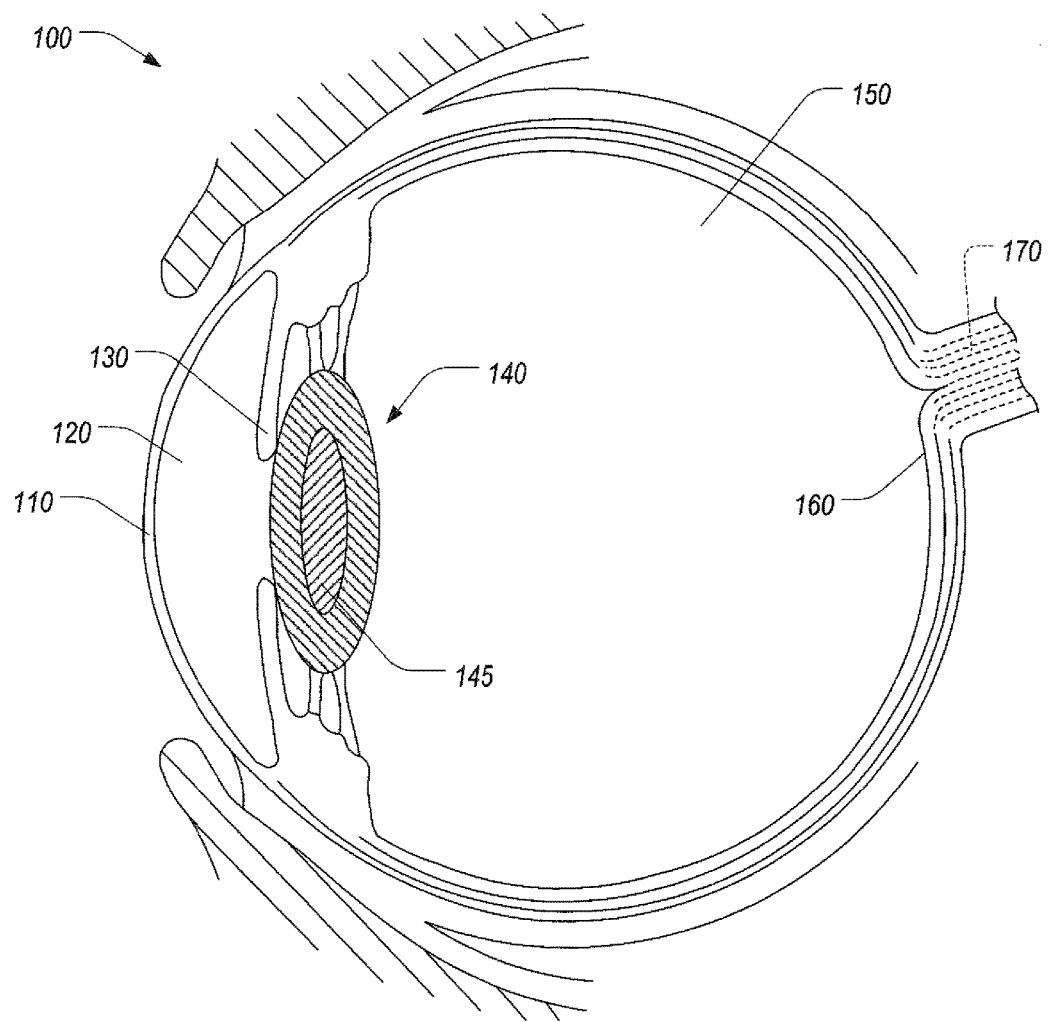
FIG. 1 illustrates a diagram of a human eye illustrating various parts of the eye.

FIG. 1 is a schematic drawing of a human eye 100. Light enters the eye from the left of FIG. 1, and passes through the cornea 110, the anterior chamber 120, a pupil defined by the iris 130, and enters lens 140. After passing through the lens 140, light passes through the vitreous chamber 150, and strikes the retina 160, which detects the light and converts it to a signal transmitted through the optic nerve 170 to the brain (not shown).

Laser cataract surgery involves the removal of an opacified crystalline lens 140 through an incision in the cornea 110. During laser cataract surgery, a laser can be used to segment and fragment a portion of the lens 140 for removal through the corneal incision. The nucleus 145 of the cataract can be a region of the lens which is harder than the surrounding lens 140. It may be advantageous, as described here, to deliver a greater amount of laser energy to points within the nucleus 145 for effective tissue separation and fragmentation.

Described below are systems and methods used to determine a laser treatment plan and to perform laser lens fragmentation according to the treatment plan. Determining the treatment plan can include, for example, mapping regions of the lens for delivery of laser energy with varying numerical apertures. For example, two zones can be defined in the treatment plan where a laser beam with a first numerical aperture and a first energy is delivered to the first zone and the laser beam with a second numerical aperture and a second energy is delivered to the second zone. As described in further detail here, any number of zones can be defined in the treatment plan, and, in some embodiments, a continuously variable numerical aperture can be used to deliver laser energy where the laser beam has a numerical aperture and laser energy that are substantially continuous functions of position within the lens 140.

Figure 2A:
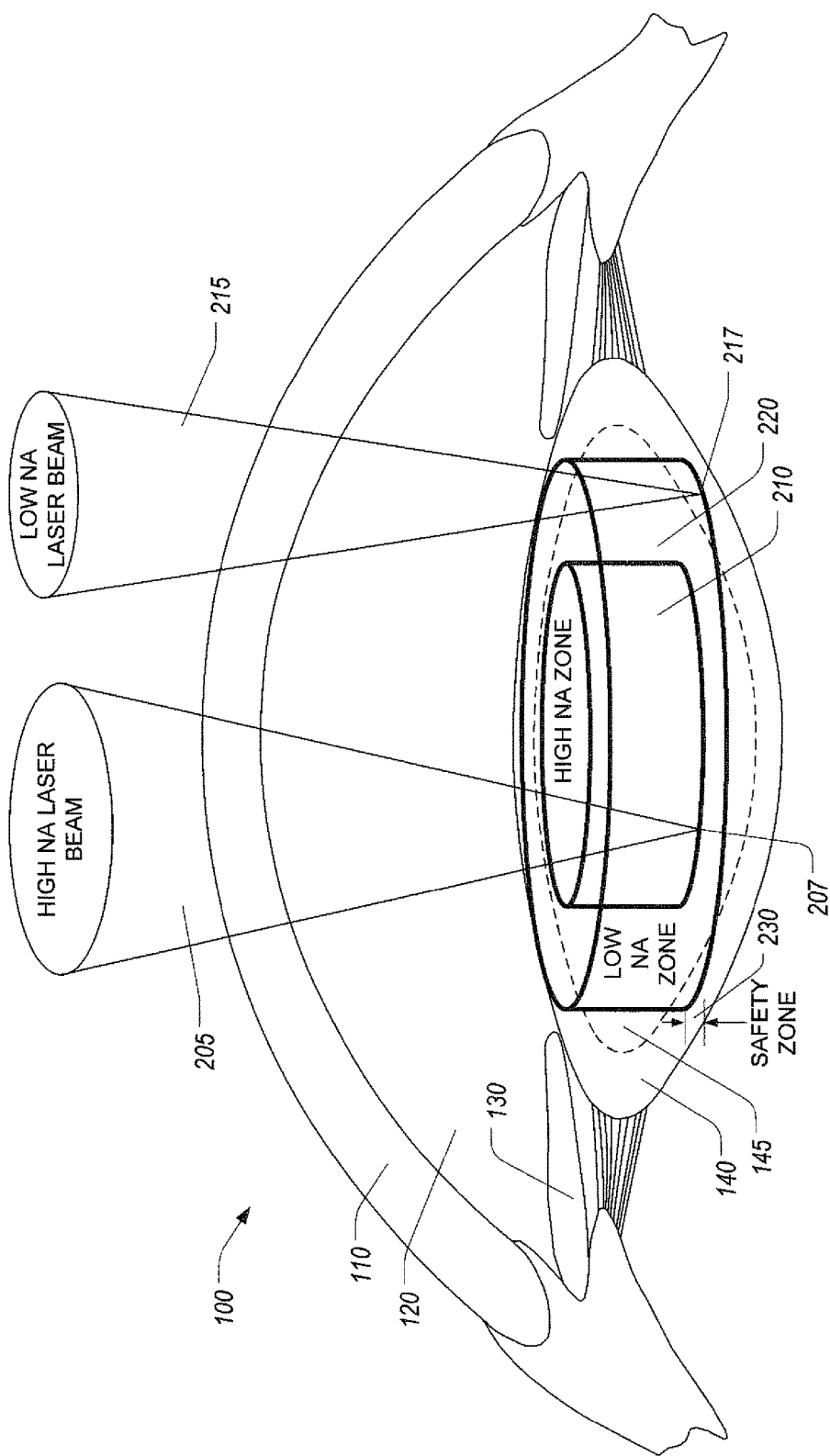
FIG. 2A illustrates a representation of performing a lens fragmentation procedure using a varying numerical aperture.

FIG. 2A illustrates a representation of a laser lens fragmentation procedure performed using laser beam with different numerical apertures in different regions of the lens. A cross-section view of the eye 100 is shown along with the cornea 110, the anterior chamber 120, the iris 130, and the lens 140 having lens nucleus 145. The illustration also shows a representation of a laser beam 205 with a relatively high NA and a laser beam 215 with a relatively low numerical aperture. The high NA laser beam 205 is shown to have a focus at a point 207 within a high NA zone 210. The low NA laser beam 215 is shown to have a focus at a point 217 within a low NA zone 220. A safety zone 230 is also shown where the safety zone is designated as a region in the lens 140 where focused laser energy is not delivered.

The laser lens fragmentation procedure, as shown, defines two regions within the lens for receiving laser beams of different numerical apertures. The high NA zone 210 comprises a central portion of the lens 140. The high NA zone 210 can include at least a portion of the lens nucleus 145 where the lens tissue is often harder and more difficult to fragment or cut. The high NA zone 210 can be determined by analyzing a structure of the patient's eye, as described here. The high NA zone 210 is shown to be substantially cylindrical, but other shapes may be appropriate including ellipsoids, spheres, cubes, irregular shapes, and the like. For example, based at least in part on an analysis of the patient's eye and the cataract, the high NA zone 210 can be defined to cover portions of the cataract expected to be harder than other portions. The high NA zone 210 can include these areas so that the high NA laser beam 205 can be used to fragment, crack, or cut these portions of tissue because a greater energy can be delivered through the high NA laser beam 205. The high NA laser beam 205 can have a numerical aperture that is at least about 0.2 and/or less than or equal to about 0.6, at least about 0.25 and/or less than or equal to about 0.55, at least about 0.3 and/or less than or equal to about 0.5, or at least about 0.3 and less than or equal to about 0.4.

The low NA zone 220 comprises a peripheral region surrounding the high NA zone 210. The low NA zone 220 can be configured to be radially closer to the iris 130, as measure from a central portion of the lens 140 or eye. This region may be softer and/or easier to cut relative to the central portion of the lens 140 or the lens nucleus 145. As described here with reference to FIGS. 2B and 2C, the low NA laser beam 215 may be delivered using an energy that is less than the energy of the high NA laser beam 205 and still sufficiently fragment the lens for removal. In some embodiments, the lower energy is used due in part to safety considerations related to laser energy on the retina 160, as described in greater detail with reference to FIG. 2B. The low NA laser beam 215 may be advantageously configured to fragment the lens in a zone that is radially further from the center of the lens 140 compared to the high NA zone 210, allowing for a larger volume to be fragmented as described here with reference to FIG. 2C. By reducing the numerical aperture of the laser beam, the amount of energy delivered to the retina increases for a given laser energy. This can lead to damage to the retina if the laser energy at the retina exceeds damage thresholds. In some embodiments, the laser energy can be reduced for the low NA laser beam 215 to conform to safety standards. Due in part to the material near the periphery of the lens 140 being generally softer, the reduced laser energy in the low NA beam 215 may be able to fragment the lens 140 in the low NA region 220. In some embodiments, the low NA zone 220 is annular in shape and is adjacent to the high NA zone 210. Other shapes and configurations are possible as well. The low NA zone 220 can be configured to cover, in aggregate with the high NA zone 210 and the safety zone 230, the entire treatment volume. The low NA laser beam 215 can have a numerical aperture that is at least about 0.075 and/or less than or equal to about 0.25, at least about 0.1 and/or less than or equal to about 0.2, at least about 0.125 and/or less than or equal to about 0.175, or at least about 0.125 and less than or equal to about 0.15.

The safety zone 230 comprises a region of the lens that is designated to not receive any focused laser radiation during lens fragmentation. The safety zone 230 can be defined as a boundary around the edge of the lens 140 configured to provide a buffer zone to reduce or eliminate potential damage to the anterior lens capsule, the posterior lens capsule, and/or the iris. The safety zone 230 can be for example, about 0.5 mm inwards from the iris edges, from the anterior lens capsule, and/or the posterior lens capsule. In some embodiments, the safety zone is at least about 0.1 mm and/or less than or equal to about 2 mm from these structures, at least about 0.25 mm and/or less than or equal to about 1 mm from these structures, or at least about 0.3 mm and/or less than or equal to about 0.75 mm from these structures.

Changing the numerical aperture of the laser beam can change the energy delivered at the focal region for a given laser energy (e.g., a constant pulse energy in a pulsed laser system). For a given laser energy, the energy at the high NA focus 207 will be greater than the energy at the low NA focus 217 by a factor, where the factor is roughly equal to the square of the ratio of the high numerical aperture to the low numerical aperture. For example, if the high NA laser beam 205 has a numerical aperture of about 0.3 and the low NA laser beam 215 has a numerical aperture of about 0.15, the energy delivered to the high NA focus spot 207 is roughly four times the energy delivered to the low NA focus spot 217 for a given laser energy. Accordingly, compared to systems with a fixed numerical aperture laser beam with a relatively low NA, the systems and methods here can be configured to deliver a greater laser energy to the lens nucleus 145 which may be advantageous to fragment high grade nuclear cataracts. As a specific example, Table 1 compares the energy threshold for lens tissue separation for a NA of 0.4 and a NA of 0.12 for different spot-line sizes. It can be seen that high NA can use less energy to achieve lens tissue separation when compared to low NA.

| Spot-Line | NA = 0.4 | NA = 0.12 |
| --- | --- | --- |
| 5 µm × 5 µm | 1.5 µJ | >8 µJ |
| 6 µm × 6 µm | 1.5 µJ | >8 µJ |
| 7 µm × 7 µm | 2.0 µJ | >8 µJ |
| 8 µm × 8 µm | 3.0 µJ | >8 µJ |
| 9 µm × 9 µm | 3.5 µJ | >8 µJ |
| 10 µm × 10 µm | 7.5 µJ | >8 µJ |

Figure 2B:
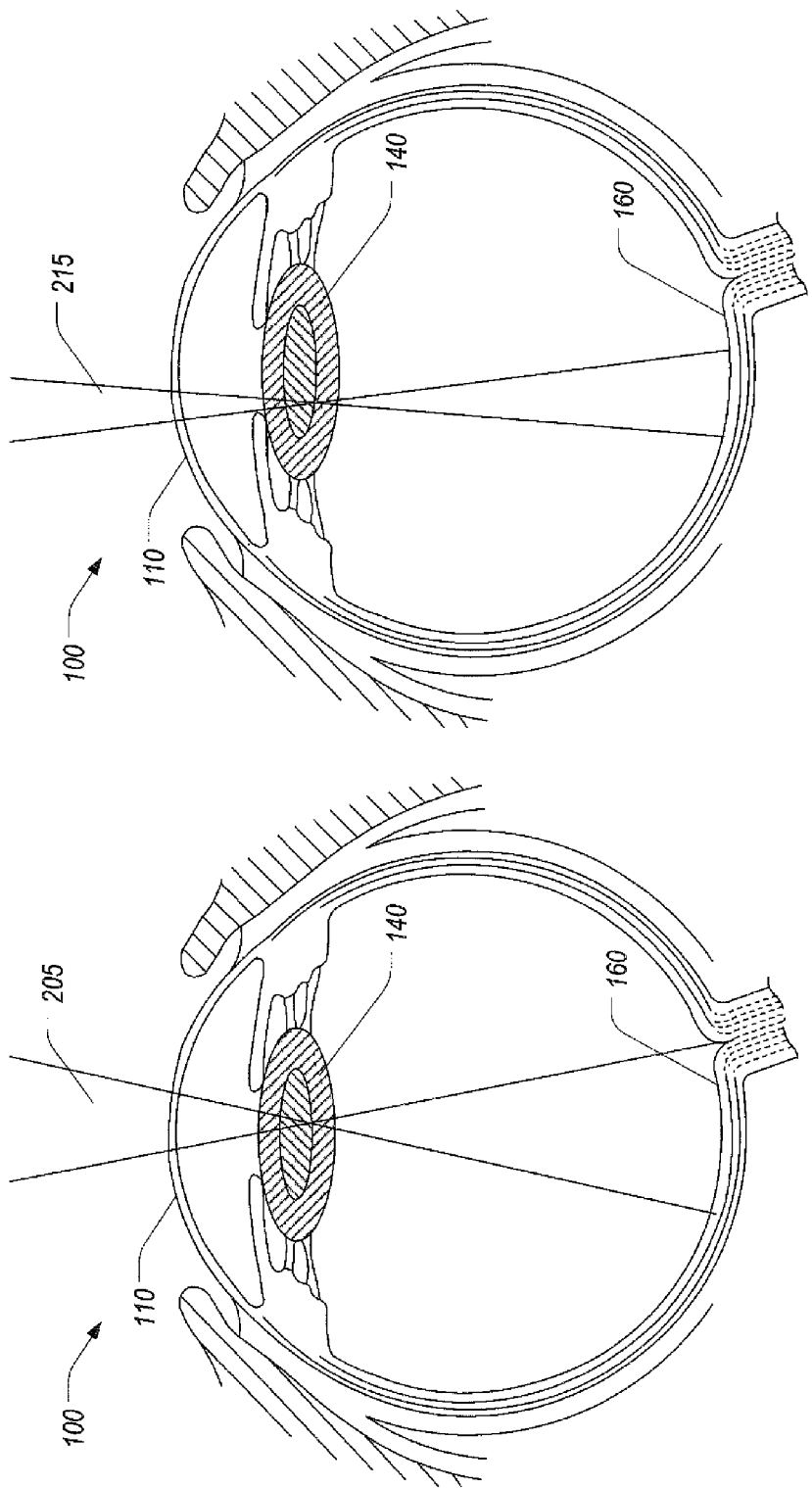
FIG. 2B illustrates a representation of laser energy delivered to a retina for laser beams having different numerical apertures.

One limitation on the energy that can be used in a laser system used to perform laser lens fragmentation is based at least in part on safety standards related to the amount of energy delivered to a patient's retina. FIG. 2B illustrates a representation of laser energy delivered to a retina 160 for laser beams having different numerical apertures. The illustration on the left shows that for a high NA laser beam 205 the laser energy delivered to the retina 160 is spread out over a larger area when compared to the illustration on the right depicting a low NA laser beam 215. For a given laser energy, this means that the amount of energy delivered to the retina 160 decreases with an increase in numerical aperture. The maximum laser exposure at the retina 160 is approximately proportional to $1/NA^2$. Accordingly, for a given maximum laser exposure, the high NA laser beam 205 can have an energy that is greater than the low NA laser beam 215. For example, if the high NA laser beam 205 has a numerical aperture of about 0.3 and the low NA laser beam 215 has a numerical aperture of about 0.15, the high NA laser beam 205 can have an energy that is roughly four times greater than the low NA laser beam 215 and deliver roughly the same maximum laser energy to the retina 160. Combining this with the laser focus energy considerations above, means that using the high NA laser beam 205 within the high NA zone 210 and the low NA laser beam 215 in the low NA zone 220 can result the energy being delivered to the high NA focus 207 being a factor of $NA^4$ greater than the energy being delivered to the low NA focus 217 while abiding by safety standards.

The safety standards can be based on concerns with damaging a retina or other areas of the patient's eye. The damage may arise from thermal effects, microbubble formation, mechanical shockwave damage from overheating melanosomes, or other similar effects. Regulatory bodies, lawmakers, or other standards-setting organizations establish guidelines for defining a recommended amount of power delivered to reduce or minimize potential damage to the patient's eye. For example, ANSI standard Z136.1-2007 and ISO 15004-2:2007 provide guidance for the safe use of lasers, and have been used to set safety standards for laser use in medical devices, such as ophthalmic surgical systems. These standards can be subject to model-dependent calculations, depending on laser wavelength, retinal beam radius, laser pulse duration, laser pulse frequency, and the like. For example, in laser cataract surgery using an ultra-short pulsed laser, the safety guidelines suggest that for a pulse rate greater than about 20 kHz, a wavelength of between about 1030 nm and about 1064 nm, the derived maximum permissible exposure (MPE) for retina safety is about $9.4*t^{(-0.25)}$ W/cm$^2$, where t is the laser exposure time. The peak intensity at the retina, which is inversely proportional to the square of the numerical aperture, should be configured to be lower than the derived MPE. Thus, in some embodiments, the numerical aperture and laser energy can be selected to conform to a safety threshold, such as the derived MPE.

Figure 2C:
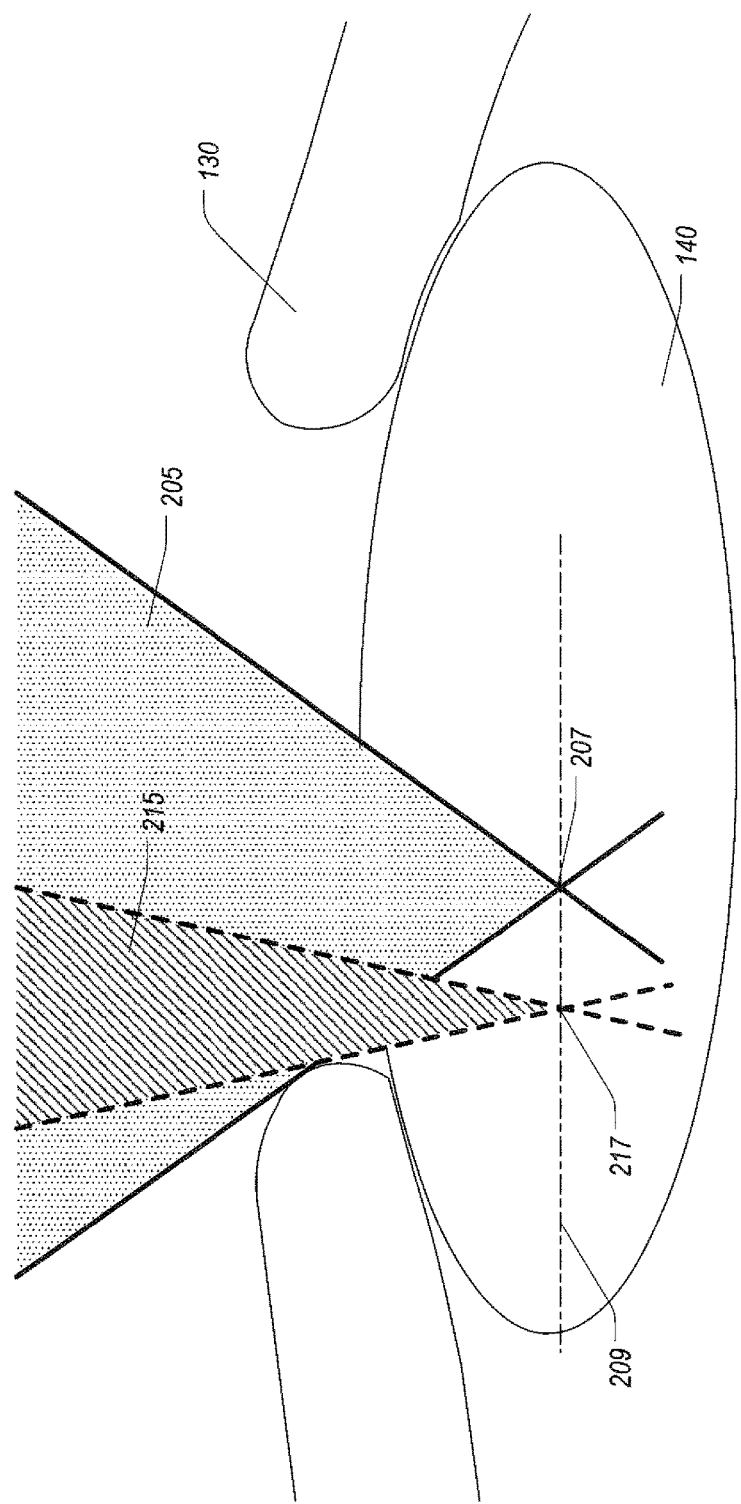
FIG. 2C illustrates a representation of a shadowing of the iris for laser beams having different numerical apertures.

Another factor in determining a laser treatment plan is a planned treatment volume. FIG. 2C illustrates a representation of shadowing by the iris for laser beams having different numerical apertures. It may be desirable or advantageous to avoid delivering laser energy to the iris 130 to reduce or eliminate potential injury to the iris 130. A laser beam with a higher NA has a larger opening angle, forming a cone that is broader than a laser beam with a lower NA. The illustration shows the high NA laser beam 205 with the high NA focus 207 and the low NA laser beam 215 with the low NA focus 217 at roughly the same depth 209 behind the iris 130. At this depth, the position of the high NA focus 207 is radially closer to the center of the lens 140 compared to the low NA focus 217. The high NA laser beam 205 would contact the iris 130 if it were to move to the left in the illustration. Thus, the treatment volume for the high NA laser beam 205 would not be able to include points more peripheral than the point represented by the high NA focus 207. It may be desirable, however, to extend the treatment volume towards the iris 130. This can be accomplished, as illustrated, by lowering the numerical aperture of the laser beam. For example, the low NA laser beam 215 can be focused at low NA focus 217, which is more peripheral than the high NA focus 207. Accordingly, referring back to FIG. 2A, the high NA zone 210 can include all points that are radially closer to the center of the lens than the high NA focus 207 shown in FIG. 2C. Similarly, referring back to FIG. 2A, the low NA zone 220 can include all points that are radially closer to the center of the lens than the low NA focus 217 and that are radially further from the lens than the high NA focus. As described here, the shapes or configurations of the various zones associated with laser beams of varying numerical apertures need not be cylindrical or annular. In some embodiments, the shadowing of the iris 130 can result in the shape of a zone to be circular at a particular depth, which is based on the geometry of the patient's eye.

In some embodiments, when formulating a treatment plan for laser lens fragmentation, multiple treatment zones can be identified, determined, and/or delineated. The various treatment zones can be based at least in part on some combination of safety considerations, iris shadowing, cataract characteristics (e.g., cataract grade), a structure of the patient's eye, a desired or selected amount of energy to deliver to a location, and the like. As described, the treatment plan included identifying two zones for laser delivery using two numerical apertures. In some embodiments, the treatment plan can include three zones, four zones, five zones, six zones, or more than six zones. In some embodiments, the treatment plan can include using three numerical apertures, four numerical apertures, five numerical apertures, six numerical apertures, or more than six numerical apertures. In some embodiments, the treatment plan can include a planned or desired laser energy and/or numerical aperture as a function of position within the lens 140. The function can be substantially continuous or it can be discrete, having any number of suitable steps in value as a function of position.

The treatment plan can vary with depth within the lens and/or as a function of radial position from a central axis through the lens 140.

In some embodiments, the laser lens fragmentation methods and systems described here can be used to reduce an amount of CDE during phacoemulsification. In some embodiments, the reduction in the amount of CDE during phacoemulsification for grade 3 cataracts can be greater than about 50%, greater than about 60%, greater than about 70%, greater than about 80%, greater than about 90%, or about 100%. In some embodiments, the step of performing phacoemulsification can be eliminated through the use of the systems and methods described here. For example, sufficient laser energy can be delivered to a lens to sufficiently cut the lens such that the fragmented lens can be aspirated without applying any ultrasonic energy. This can advantageously remove the phacoemulsification step, which can be the only step in a laser cataract procedure that involves the application of energy not from a laser. Thus, in some embodiments, the entire laser cataract surgery can be performed using laser energy. Typical systems are configured to soften lenses for phacoemulsification, and have been shown to be unable to crack high grade cataracts. For example, performing laser lens fragmentation on a grade 3 or grade 4 nuclear cataract with a typical system, phacoemulsification is still required after application of the laser to fully remove the desired portion of the lens. Using some embodiments of the systems and methods described here, grade 3 and/or grade 4 nuclear cataracts can be sufficiently fragmented such that they can be aspirated with no phacoemulsification, resulting in a 100% reduction in CDE.

In addition, the systems and methods described here can increase the energy parameter space available to surgeons performing cataract surgery. Due at least in part to the higher available energies for use in high NA zones, there is a greater range of energies a surgeon can use when performing laser lens fragmentation. This can provide an ability to fragment the lens more effectively and/or more efficiently.

Laser Systems

Figure 3A:
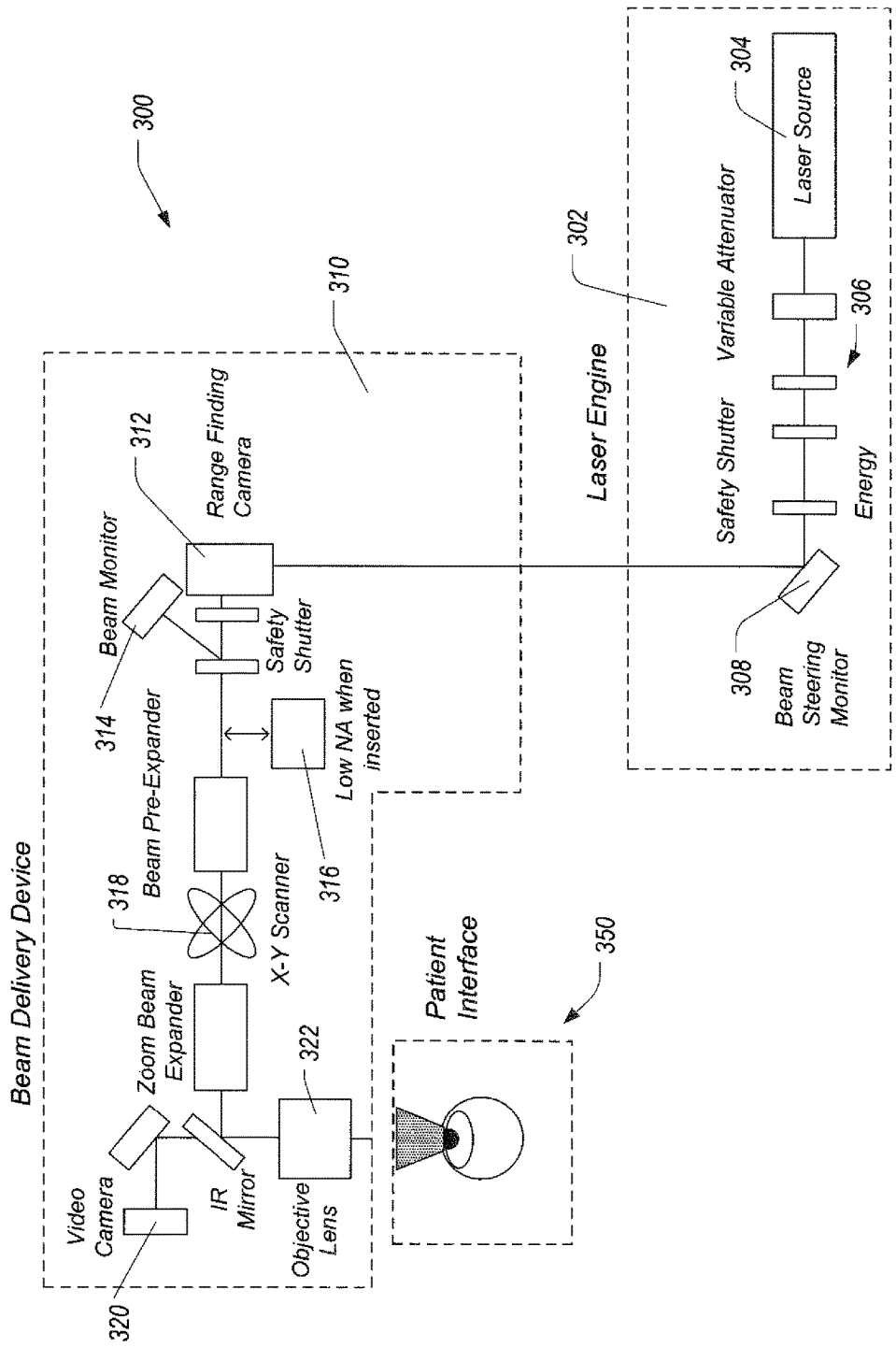
FIGS. 3A-3C illustrate example laser systems that can be used to provide a varying numerical aperture for use with some embodiments of a lens fragmentation procedure.
Figure 3B:
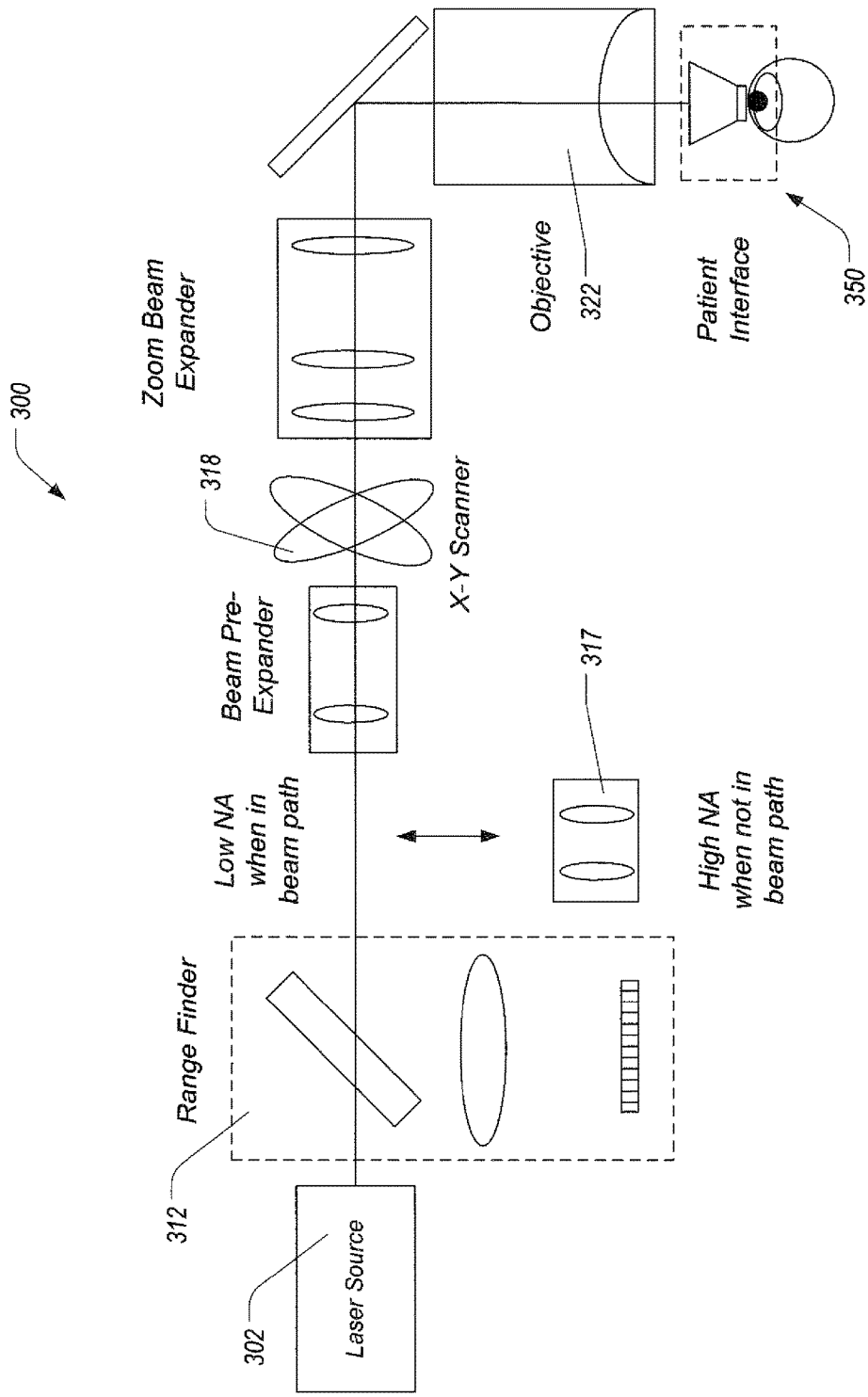
Figure 3C:
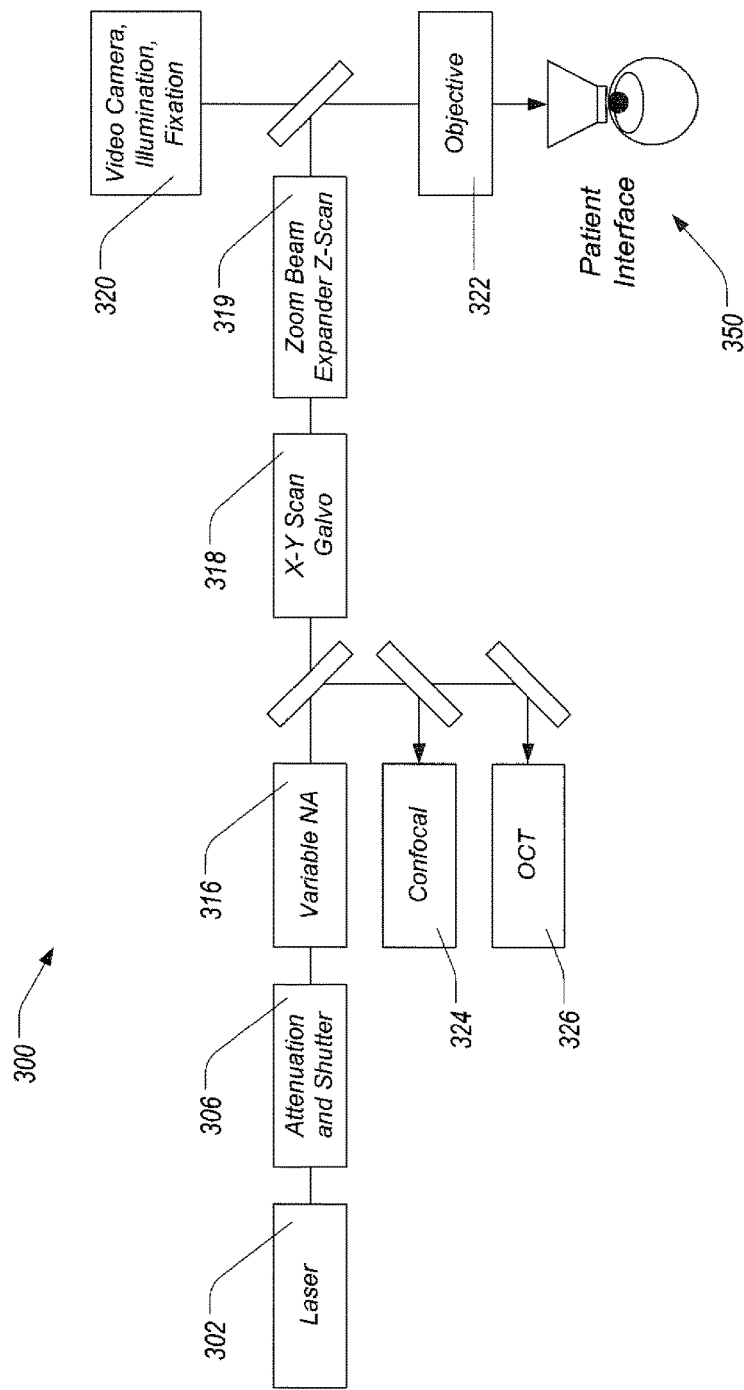

FIGS. 3A-3C illustrate example laser systems 300 that can be used to provide a varying numerical aperture for use with some embodiments of a lens fragmentation procedure. The laser systems 300 can be configured to provide two numerical apertures, three numerical apertures, ten numerical apertures, or any number of numerical apertures including a substantially continuous range of numerical apertures within functional limits of the various systems. The laser systems 300 can be pulsed laser systems, such as, for example, femtosecond lasers or picosecond lasers. Other pulse widths may be suitable as well. The laser systems 300 can be configured to deliver near infrared light. Other wavelengths may be used as well. The laser systems 300 can be configured to deliver laser light focused at a focus depth which may be controlled by the system. In some embodiments, the lasers 300 include imaging systems as well, such as video imaging and/or optical coherence tomography. The laser systems 300 can be used in conjunction with a patient interface 350. In some embodiments, the patient interface 350 can be a liquid interface configured to substantially maintain a shape of the patient's eye while maintaining it in substantially the same location and/or orientation. Any suitable patient interface 350 can be used including, for example, liquid interfaces, applanation lenses, deformable contact lenses, or no patient interface.

In some embodiments, a pulsed laser (e.g. a femtosecond laser) can be used to segment and fragment a lens by ablating a pattern onto the targeted area of the lens. The lens segmentation and fragmentation can be accomplished through a variety of methods and generally include, for example, determining areas or patterns to cut on the lens, selecting laser energies, selecting or determining a numerical aperture to use for cutting the various areas of the lens, and delivering the laser beam having the determined energy and/or numerical aperture to spots along the designated cut locations. The energy, frequency and the duty cycle of the pulsed lasers can be varied to produce laser segmentation or fragmentation that is sized and shaped to remove the diseased lens from the patient's eye.

FIG. 3A illustrates a laser system comprising a laser engine 302 and a beam delivery device 330. The laser engine 302 can be configured to generate the laser pulses used for laser lens fragmentation. The laser engine 302 can include a laser source 304, optical components 306, and a beam steering monitor 308. The components of the laser engine 302 can be configured to generate the desired laser pulse of a desired energy.

The laser system 300 can include a beam delivery device 310 configured to adjust properties of the laser pulse prior to delivery to the patient at the patient interface 350. The beam delivery device 310 can include a range finding camera 312 that can be configured to determine a lens surface and/or orientation. The range finding camera 312 can be configured to determine a depth of the anterior chamber and a location of the lens relative to the anterior chamber of the patient's eye. The beam delivery device 310 can include a beam monitor 314 configured to provide feedback related to properties of the laser as delivered by the laser engine 302.

To change a numerical aperture of the laser beam, the beam delivery device 310 can include a mechanism for switching between a high numerical aperture and a low numerical aperture. The beam delivery device 310 can include a low NA insert 316 that, when inserted into the beam path, changes the numerical aperture of the laser beam to be a relatively low numerical aperture. When the low NA insert 316 is out of the beam path, the laser beam can be configured to deliver a laser beam with a relatively high numerical aperture.

The beam delivery device 310 includes an x-y shutter 318 configured to scan the laser beam across two dimensions. In some embodiments, the two dimensions can be parallel to the iris. In some embodiments, the two dimensions can lie in another direction.

The beam delivery device 310 can include a video camera 320 configured to provide visual feedback regarding the target, the laser beam, or both. The beam delivery device can include an objective lens 322 configured to focus the laser beam to a spot. During laser lens fragmentation, the objective 322 can be configured to focus the laser spot within the lens to ablate, cut, or fragment the lens tissue.

FIG. 3B illustrates another example embodiment of a dual-NA laser system 300 configured to deliver a pulsed laser to a targeted lens of a patient. Similar to the laser system in FIG. 3A, the laser system 300 includes a laser source 302, range finder 312, X-Y scanner 318, and an objective 322. These components perform generally the same functions as the laser system in FIG. 3A.

The laser system 300 of FIG. 3B includes a high NA insert 317 that is configured to generate a laser beam with a high numerical aperture when it is in the beam path. When the high NA insert 317 is not in the beam path, the laser system 300 is configured to deliver a laser beam with a low numerical aperture.

The laser systems 300 of FIGS. 3A and 3B can be configured to rapidly switch between a low NA laser beam and a high NA laser beam. For example, the low NA insert 316 of FIG. 3A or the high NA insert 317 of FIG. 3B can be configured to be switched in and out of the beam path with a typical time of about 1 us or less. In some embodiments, the low NA insert 318, the high NA insert 317, or both can include a waveplate that can be opto-mechanically switched such that in a first configuration, the laser beam is polarized in such a way that optical elements selectively deliver a laser beam with a high NA to the objective 322, and in a second configuration, the laser beam is polarized in such a way that the optical elements selectively deliver a laser beam with a low NA to the objective 322. Other methods of numerical aperture switching is possible, such as electro-mechanical switching, optical switching, polarization switching, and the like.

FIG. 3C illustrates a laser system 300 that is configured to provide a substantially continuously variable numerical aperture. The laser system 300 includes a laser 302 and optical elements 306 along with X-Y scan galvanometer mirrors 318, and an objective 322. The laser system 300 includes a video camera, illumination, or fixation system 320 configured to provide light, video feedback, or other information about the laser beam. The laser 300 includes a zoom beam expander z-scan configured to adjust the beam width and to adjust a depth of focus.

The laser system 300 includes the variable NA module 316 that is configured to provide a substantially continuously variable NA over a range of numerical apertures. The variable NA module 316 can include optical components, electrical components, and/or mechanical components configured to continuously adjust beam parameters to provide a substantially continuous variable numerical aperture. For example, the variable NA module 316 can be a telescope that includes a plurality of lenses configured to move relative to each other and to provide a variable numerical aperture.

The laser system 300 includes a confocal module 324 configured to provide depth-selection capabilities to the laser system 300. The laser system 300 includes an OCT module 326 configured to provide optical coherence tomography images to the system 300. These images can be used to generate images of the patient's eye, to determine the geometry of the patient's eye, and/or to generate laser treatment plans based on the images of the patient's eye.

Example Laser Cataract Surgery Control System

Figure 4:
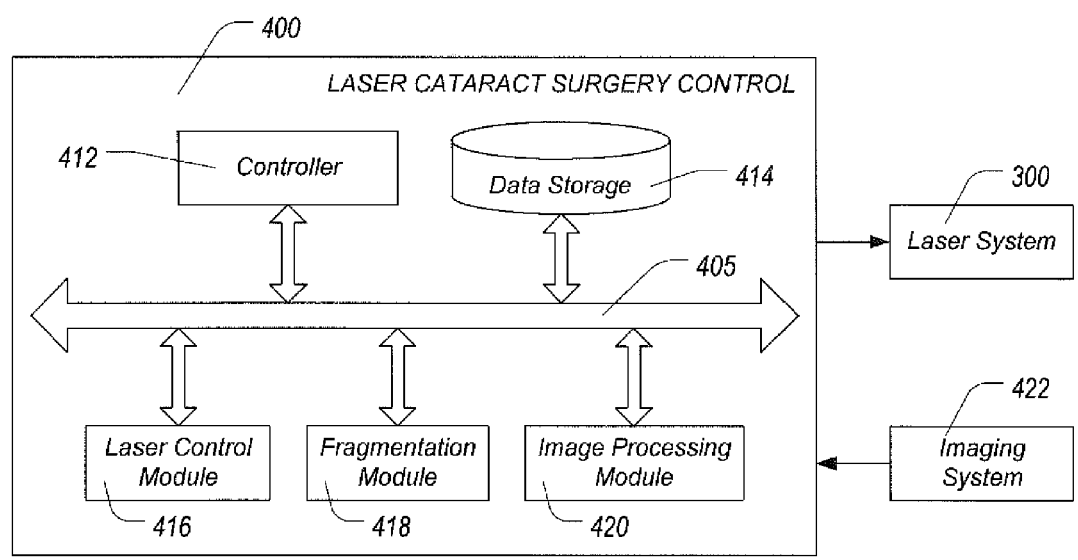
FIG. 4 illustrates an example laser cataract surgery control system.

FIG. 4 illustrates a block diagram of an example laser cataract surgery control system 400 in communication with a laser system 300 and an imaging system 422. The laser cataract surgery control system 400 can be configured to determine treatment regions within a lens of a patient, to determine a safety zone within the lens, to determine a numerical aperture of a laser beam to deliver to identified treatment regions, to determine a laser energy to deliver to the treatment regions, to receive image data from the imaging system 422, to analyze the received image data, to control the laser system 300 to deliver laser energy as determined by the system 400, and the like.

The laser cataract surgery control system 400 includes a controller 412, data storage 414, a laser control module 416, a fragmentation module 418, and an image processing module 420. The various components of the laser cataract surgery control system 400 can communicate with external systems and each other using communication bus 405. Communication between the laser cataract surgery control system 400, the laser system 300, and/or the imaging system 422 can occur using wired or wireless communication, and using any suitable protocol.

The controller 412 can include hardware, software, and/or firmware components used to control the laser cataract surgery control 400. The controller 412 can be configured to receive information from the imaging system 422, to receive user input from a user interface component, to determine treatment zones, and to determine laser parameters. The controller 412 can include modules configured to control the attached components and analyze received information. The controller 412 can include one or more physical processors and can be used by any of the modules within the system 400 to process information. The laser cataract surgery control 400 can include data storage 414 for storing received information, control parameters, executable programs, and other such information. Data storage 414 can include physical memory configured to store digital information and can be coupled to the other components of the laser cataract surgery control system 400.

The laser cataract surgery control system 400 includes the image processing module 420. The image processing module 420 can be configured to receive image information from the imaging system 422, from data storage 414, and/or from user input. The image processing module 420 can be configured to analyze the received images to determine structures of the eye and their associated locations and/or sizes. For example, the image processing module 420 can determine a pupil of the patient's eye, the lens, the cornea, and the like with their sizes and/or locations. The image processing module 420 can be configured to provide real-time feedback to the control system 400 to adjust laser delivery based at least in part on changes to the patient's eye. The image processing module 420 can be configured to provide information regarding the laser beam being delivered to the patient where the information can be used as feedback in the laser control module 416 to adjust laser delivery properties based at least in part on the feedback information. The imaging system 422 can be any suitable imaging system for use with a laser cataract surgery system 400 including, but not limited to, OCT systems, video cameras, LCI systems, or other similar systems. The imaging system 422 can deliver real-time image data to the control system 400 for processing, or the image data can be provided not in real time. The laser cataract surgery control system 400 can be configured to operate without image data from the imaging system 422, or without analyzing any image data. For example, a user can use the laser cataract surgery control to perform laser lens fragmentation without the control system 400 analyzing image data and/or without the control system 400 determining structures within the patient's eye. In some embodiments, a user identifies properties of the patient's eye and inputs this information into the control system 400.

The laser cataract surgery control 400 includes the fragmentation module 418. The fragmentation module 418 can be configured to determine regions within the lens for laser delivery. For example, the fragmentation module can determine a safety zone where no focused radiation is to be delivered and fragmentation zones where focused laser radiation is to be delivered. Within the fragmentation zones, the fragmentation module 418 can use the controller 412 to determine a high NA zone and a low NA zone. The high NA zone, as described here, can be the zone of the lens where the laser system 300 will deliver a high NA beam. Similarly, the low NA zone can be the zone of the lens where the laser system 300 will deliver a low NA beam. The fragmentation module 418 can be configured to determine any number of fragmentation zones.

The fragmentation module 418 can be configured to receive information regarding the structure of the patient's eye from the image processing module 420, a user input system, another external system, or any combination of these. Based at least in part on the image analysis information, the fragmentation module 418 can determine a treatment plan or treatment algorithm that includes planned fragmentation locations, fragmentation patterns, fragmentation depths, fragmentation volumes, and the like. For example, the fragmentation module 418 can determine to use a pie-cut treatment (e.g., cuts extending radially outward from a central location), a grid treatment (e.g., cuts extending along substantially straight lines along vertical and/or horizontal directions), or some other treatment. The treatment can be determined by the fragmentation module 418 or it can be selected by a user. The fragmentation module 418 can develop a treatment plan with details related to a size of the cuts, a distance between laser pulses, the energy of the laser pulses, and the like.

The fragmentation module 418 can be configured to determine a numerical aperture for the laser beam being delivered to a particular fragmentation zone. As described here, the numerical aperture can be selected based on safety considerations, iris shadowing, cataract hardness, cataract location, laser system properties, and the like. In some embodiments, the fragmentation module 418 is configured to determine a first treatment zone to be treated by a laser beam with a relatively high numerical aperture. The fragmentation module 418 can be configured to determine a maximum size of this region based at least in part on iris shadowing effects. The fragmentation module 418 can then be configured to select a laser energy for delivery to this region. In some embodiments, the laser energy is a fixed value or is selected from a range of values that is independent from the selection of the numerical aperture and/or the fragmentation zones.

An example of a determination of fragmentation zones is shown in Table 1. Table 1 shows allowed lateral dimensions for lens fragmentation relative to pupil diameter. In the table, a safety zone of 0.5 mm on the edge of the pupil is used. As an example, using a pupil diameter of 7.5 mm, a laser beam with a numerical aperture of 0.3 can be made to fragment a lens where the fragmentation can occur over an area with a diameter of about 4.7 mm at a depth of about 4 mm from the pupil. A low NA laser beam can then be used to fragment the lens out to about a 5.8 mm diameter.

TABLE 1 lens fragmentation lateral dimension at a depth H = 4.0 mm

| d (mm), lens frag. diameter at depth H | NA | | | | | | | |
|---|---|---|---|---|---|---|---|---|
| | 0.125 | 0.2 | 0.25 | 0.30 | 0.35 | 0.40 | 0.45 | 0.50 |
| Pupil diameter (mm) 5.0 | 3.3 | 2.8 | 2.5 | 2.2 | 1.9 | 1.6 | 1.3 | 0.9 |
| 5.5 | 3.8 | 3.3 | 3.0 | 2.7 | 2.4 | 2.1 | 1.8 | 1.4 |
| 6.0 | 4.3 | 3.8 | 3.5 | 3.2 | 2.9 | 2.6 | 2.3 | 1.9 |
| 6.5 | 4.8 | 4.3 | 4.0 | 3.7 | 3.4 | 3.1 | 2.8 | 2.4 |
| 7.0 | 5.3 | 4.8 | 4.5 | 4.2 | 3.9 | 3.6 | 3.3 | 2.9 |
| 7.5 | 5.8 | 5.3 | 5.0 | 4.7 | 4.4 | 4.1 | 3.8 | 3.4 |
| 8.0 | 6.3 | 5.8 | 5.5 | 5.2 | 4.9 | 4.6 | 4.3 | 3.9 |
| 8.5 | 6.8 | 6.3 | 6.0 | 5.7 | 5.4 | 5.1 | 4.8 | 4.4 |
| 9.0 | 7.3 | 6.8 | 6.5 | 6.2 | 5.9 | 5.6 | 5.3 | 4.9 |
| 9.5 | 7.8 | 7.3 | 7.0 | 6.7 | 6.4 | 6.1 | 5.8 | 5.4 |
| 10.0 | 8.3 | 7.8 | 7.5 | 7.2 | 6.9 | 6.6 | 6.3 | 5.9 |

Table 1 can be derived based at least partly on geometrical and physical considerations. For example, by considering the pupil diameter, D, safety zone, S, the depth of lens fragmentation, H, the refractive index of the lens, n, and the numerical aperture, NA, the diameter of lens fragmentation, d, can be determined using the equation:

$$d = D - 2S - 2H^* \tan(\theta) \text{ where } \theta = a\sin(NA/n). \qquad (1)$$

Thus, the fragmentation module 418 can use an algorithm employing a similar equation to equation (1) and/or values as demonstrated in Table 1 to determining laser fragmentation zones.

The laser cataract surgery control system 400 includes the laser control module 416 configured to control the laser system 300, to send instruction to the laser control system 300, or to generate instructions for a user to control the laser system 300. The laser control module 416 can be configured to control the laser system 300 according to the laser parameters determined by the fragmentation module 418.

Example Laser Fragmentation Procedure

Figure 5:
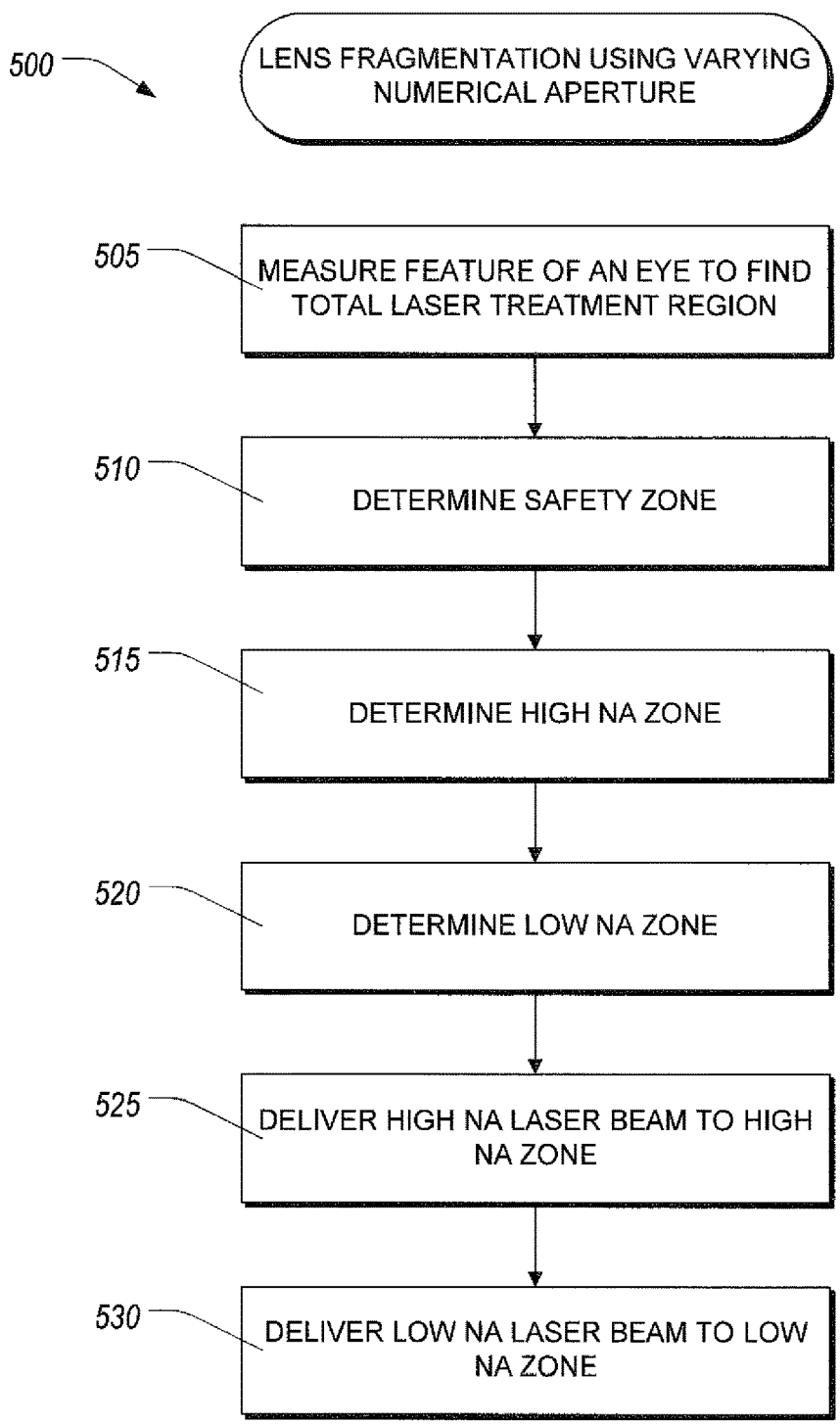
FIG. 5 illustrates a flow chart of an example laser fragmentation procedure.

FIG. 5 illustrates a flow chart of an example method 500 for performing a laser fragmentation procedure using a varying numerical aperture laser beam. The method 500 can be performed by any of the systems described here, including the laser cataract surgery control system 400 described with reference to FIG. 4. For ease of description, the method 500 will be described as being performed by a surgery control system, which can be similar to the control system 400. However, any step or combination of steps of the method 500 can be performed by any system or combination of systems or system components.

In block 505, the surgery control system measures features of an eye of a patient to find a total laser treatment region. The surgery control system can measure the features based at least in part on real-time measurements involving surgeon input, image analysis, or both. In some embodiments, the surgery control system determines, for example, a size or location of the patient's pupil (e.g., a pupil diameter), a size or location of the patient's lens, a size or location of the patient's cornea, an anterior boundary of the lens, a posterior boundary of the lens, or any combination of these.

In block 510, the surgery control system determines a safety zone comprising a region of the eye of the patient which will not receive focused laser radiation. The safety zone can be a region of the lens of the patient's eye comprising a volume that is a selected distance from structures within the patient's eye. For example, the safety zone can be defined as a distance inwards from an edge of an iris of the patient's eye, a distance from an anterior lens capsule, and a distance from a posterior lens capsule. The distance can be, for example, at least about 0.1 mm and/or less than or equal to about 2 mm from these structures, at least about 0.25 mm and/or less than or equal to about 1 mm from these structures, or at least about 0.3 mm and/or less than or equal to about 0.75 mm from these structures.

In block 515, the surgery control system determines a high NA zone, the high NA zone configured to be a region where a cone angle of a laser beam with a high numerical aperture is not shadowed by an iris of the patient's eye. The numerical aperture can be selected, for example, to conform to safety requirements and/or to result in lens tissue separation in the high NA zone. In some embodiments, the high numerical aperture is at least about 0.2 and/or less than or equal to about 0.6, at least about 0.25 and/or less than or equal to about 0.55, at least about 0.3 and/or less than or equal to about 0.5, or at least about 0.3 and less than or equal to about 0.4.

In block 520, the surgery control system determines a low NA zone, the low NA zone configured to be a region radially closer to the iris than the high NA zone where the cone angle of the laser beam with a low numerical aperture is not shadowed by the iris. In some embodiments, the high NA zone, the low NA zone, and the safety zone can be configured to occupy, in aggregate, approximately the entirety of the total laser treatment region. In some embodiments, the low numerical aperture is at least about 0.075 and/or less than or equal to about 0.25, at least about 0.1 and/or less than or equal to about 0.2, at least about 0.125 and/or less than or equal to about 0.175, or at least about 0.125 and less than or equal to about 0.15.

In some embodiments, additional zones can be determined for delivery of laser energy for laser fragmentation. As described here, the number of zones can be greater than two and the zones can be configured to each have a laser beam with a particular numerical aperture delivered thereto. As described elsewhere here, the numerical aperture and energy of the laser to be used for lens fragmentation can be represented using a substantially continuous function that is expressed as a position within the lens. In this way, a continuously variable NA laser can be used to deliver improved or optimized laser energy as a function of position to improve or maximize fragmentation within the lens.

In block 525, the surgery control system delivers the laser beam with the high numerical aperture to the high NA zone. Delivery of the high NA laser beam can be accomplished using any of the laser systems described here, such as the laser systems described with reference to FIGS. 3A, 3B, and 3C. The high NA laser beam can be configured to deliver a laser energy sufficient to cause tissue separation in the lens, and in some embodiments, to cause lens tissue separation in a grade 3 or grade 4 nuclear cataract. The high NA laser beam can be configured to deliver a maximum peak energy to a retina of the patient's eye that is less than a safety threshold.

In block 530, the surgery control system delivers the laser beam with the low numerical aperture to the low NA zone. The low NA laser beam can be configured to deliver a laser energy sufficient to cause tissue separation in the periphery of the lens. The low NA laser beam can be configured to deliver a maximum peak energy to a retina of the patient's eye that is less than a safety threshold.

In some embodiments, a position of the laser beam is tracked with a laser scanning system comprising a plurality of galvanometer mirrors. In some embodiments, delivering the laser beam includes using an electro-mechanical system to adjust a set of lens elements to adjust a numerical aperture of the laser beam when delivery of the laser beam passes between the high NA zone and the low NA zone.

In some embodiments, the laser lens fragmentation method 500 can be used to reduce or eliminate an amount of CDE during phacoemulsification. For example, the reduction in the amount of CDE during phacoemulsification for grade 3 cataracts can be greater than about 50%, greater than about 60%, greater than about 70%, greater than about 80%, greater than about 90%, or about 100%. In some embodiments, phacoemulsification can be eliminated through the use of the method 500. For example, sufficient laser energy can be delivered to a lens to sufficiently cut the lens such that the fragmented lens can be aspirated without applying any ultrasonic energy. In some embodiments, the method 500 can be used to sufficiently fragment grade 3 and/or grade 4 nuclear cataracts such that they can be aspirated with no phacoemulsification, resulting in a 100% reduction in CDE.

Much of the description here is in the context of laser lens fragmentation during laser cataract surgery. However, the systems and methods described here may be applicable to any laser treatment or surgery applied to the lens of the eye, where shadowing from the iris may affect delivery of laser energy. Furthermore, the systems and methods described here may be applicable to laser treatment of a lens in a patient's eye where retinal safety standards are a concern, where laser efficiency is a concern, and/or where efficacy of treatment is a concern. For example, refractive surgery may be performed at the lens behind the iris. For such procedures, using a varying numerical aperture during delivery of the laser may be advantageous to increase the efficiency of the procedure, to increase precision, to reduce retinal damage, and the like. As another example, lens index modification or modification of intraocular lenses can be accomplished with lasers where shadowing by the iris may affect the delivery of the laser to a target. The systems and methods described here may be used for these procedures as well. Thus, it is to be understood that the disclosed embodiments should not be restricted solely to laser lens fragmentation, and can be used for a variety of applications that deliver laser to locations behind the iris of a patient's eye.

Although the invention has been described and pictured in an exemplary form with a certain degree of particularity, it should be understood that the present disclosure of the exemplary form has been made by way of example, and that numerous changes in the details of construction and combination and arrangement of parts and steps may be made without departing from the spirit and scope of the invention as set forth in the claims hereafter.

As used here, the term "processor" refers broadly to any suitable device, logical block, module, circuit, or combination of elements for executing instructions. For example, the controller 412 can include any conventional general purpose single- or multi-chip microprocessor such as a Pentium® processor, a MIPS® processor, a Power PC® processor, AMD® processor, or an ALPHA® processor. In addition, the controller 412 can include any conventional special purpose microprocessor such as a digital signal processor. The various illustrative logical blocks, modules, and circuits described in connection with the embodiments disclosed here can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described here. Controller 412 can be implemented as a combination of computing devices, e.g., a combination of a DSP and a microprocessor, a plurality of microprocessors, one or more microprocessors in conjunction with a DSP core, or any other such configuration.

Data storage 414 can refer to electronic circuitry that allows information, typically computer or digital data, to be stored and retrieved. Data storage 414 can refer to external devices or systems, for example, disk drives or solid state drives. Data storage 414 can also refer to fast semiconductor storage (chips), for example, Random Access Memory (RAM) or various forms of Read Only Memory (ROM), which are directly connected to the communication bus or the controller 412. Other types of memory include bubble memory and core memory. Data storage 414 can be physical hardware configured to store information in a non-transitory medium.

Methods and processes described here may be embodied in, and partially or fully automated via, software code modules executed by one or more general and/or special purpose computers. The word "module" can refer to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described here can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described here may include an interface configured to permit interaction with users, operators, other systems, components, programs, and so forth.

This disclosure is provided in an exemplary form with a certain degree of particularity, and describes the best mode contemplated of carrying out the invention to enable a person skilled in the art to make and/or use embodiments of the invention. The specific ordering and combination of the processes and structures described are merely illustrative. Those skilled in the art will understand, however, that various modifications, alternative constructions, changes, and variations can be made in the system, method, and parts and steps thereof, without departing from the spirit or scope of the invention. Hence, the disclosure is not intended to be limited to the specific examples and designs that are described. Rather, it should be accorded the broadest scope consistent with the spirit, principles, and novel features disclosed as generally expressed by the following claims and their equivalents.

What is claimed is:

1. A method for fragmenting a lens of a patient's eye using a surgical laser comprising:
   measuring features of the patient's eye to find a total laser treatment region; determining:
   a safety zone comprising a region of the patient's eye that will not receive focused laser radiation;
   a high NA zone, the high numerical aperture (NA) zone comprising a region where a cone angle of a laser beam with a high numerical aperture is not shadowed by an iris of the patient's eye; and
   a low NA zone, the low NA zone comprising a region radially closer to the iris than the high NA zone where a cone angle of the laser beam with a low numerical aperture is not shadowed by the iris, the low numerical aperture being lower than the high numerical aperture; and
   delivering the laser beam with the high numerical aperture to the high NA zone, and delivering the laser beam with the low numerical aperture to the low NA zone without delivering the laser beam with the high numerical aperture to the low NA zone, wherein the high NA zone, the low NA zone, and the safety zone occupy, in aggregate, approximately an entirety of the total laser treatment region.

2. The method of claim 1, wherein the high numerical aperture is greater than or equal to 0.25.

3. The method of claim 1, wherein the low numerical aperture is less than or equal to 0.15.

4. The method of claim 1, wherein the measuring comprises measuring a pupil diameter.

5. The method of claim 1, wherein the measuring comprises measuring anterior and posterior boundaries of a lens of the patient's eye.

6. The method of claim 1, wherein the safety zone is a region of the lens of the patient's eye comprising a volume that is at least about 0.5 mm inwards from an edge of an iris of the patient's eye and at least about 0.5 mm from an anterior lens capsule and at least about 0.5 mm from a posterior lens capsule.

7. The method of claim 1, wherein a position of the laser beam is tracked with a laser scanning system comprising a plurality of galvanometer mirrors.

8. The method of claim 1, wherein delivering the laser beam comprises adjusting a set of lens elements to adjust a numerical aperture of the laser beam when delivery of the laser beam passes between the high NA zone and the low NA zone.

* * * * *